(12) United States Patent
Davis et al.

(10) Patent No.: US 7,147,761 B2
(45) Date of Patent: Dec. 12, 2006

(54) ELECTROCHEMICAL SENSOR

(75) Inventors: Brian K. Davis, Butler, PA (US);
Towner B. Scheffler, Butler, PA (US);
Louis J. Busby, Jr., Crnaberry
Township, PA (US); John F. Neighoff, Jr., Harmony, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 350 days.

(21) Appl. No.: 10/164,539

(22) Filed: Jun. 6, 2002

(65) Prior Publication Data
US 2003/0038029 A1 Feb. 27, 2003

Related U.S. Application Data

(60) Provisional application No. 60/311,909, filed on Aug. 13, 2001.

(51) Int. Cl.
*G01N 27/403* (2006.01)

(52) U.S. Cl. .................. 204/421; 204/424; 204/291

(58) Field of Classification Search ............ 204/421, 204/424, 426, 430, 431, 432, 290.01, 290.14, 204/291; 205/786.5, 794.5; 429/30, 40–44, 429/46, 128, 188, 300, 302, 305, 204, 218.1, 429/232; 252/62.2
See application file for complete search history.

(56) References Cited

U.S. PATENT DOCUMENTS 4,248,941 A * 2/1981 Louis et al. ................ 429/13
4,477,403 A * 10/1984 Pust ........................... 264/104
5,128,018 A 7/1992 Kiesele ....................... 204/415
5,331,310 A 7/1994 Stetter et al. ................ 340/632
5,392,191 A * 2/1995 Thomas et al. .............. 361/508
5,538,620 A 7/1996 Nikolskaja .................. 205/782
5,547,551 A * 8/1996 Bahar et al. ................. 204/296
6,010,606 A * 1/2000 Denton et al. ............... 204/284
6,343,003 B1 * 1/2002 Sakata et al. ............... 361/503
6,428,665 B1 8/2002 Ilic et al. .................... 204/415

FOREIGN PATENT DOCUMENTS

EP 0 543 770 A2 3/1988
EP 0 631 337 A2 6/1994
EP 0 786 660 A2 1/1997

OTHER PUBLICATIONS

Aldrich Chemical Company, Inc. Product Catalog, 1996-1997, p. 1054.*

* cited by examiner

*Primary Examiner*—Kaj K. Olsen
(74) *Attorney, Agent, or Firm*—James G. Uber; Henry E. Bartony, Jr.

(57) ABSTRACT

An electrode for use in an electrochemical sensor includes a catalyst dispersed within an electrolyte. Preferably, the catalyst is immobilized within a matrix of the electrolyte. In one embodiment, the electrode of the present invention includes at least one catalyst/electrolyte layer having a mixture of a powdered catalyst, a powdered, quasi-solid electrolyte and a binder material compressed together. The quasi-solid electrolyte can include a liquid electrolyte immobilized by a high-surface-area, high-pore-volume solid.

26 Claims, 9 Drawing Sheets

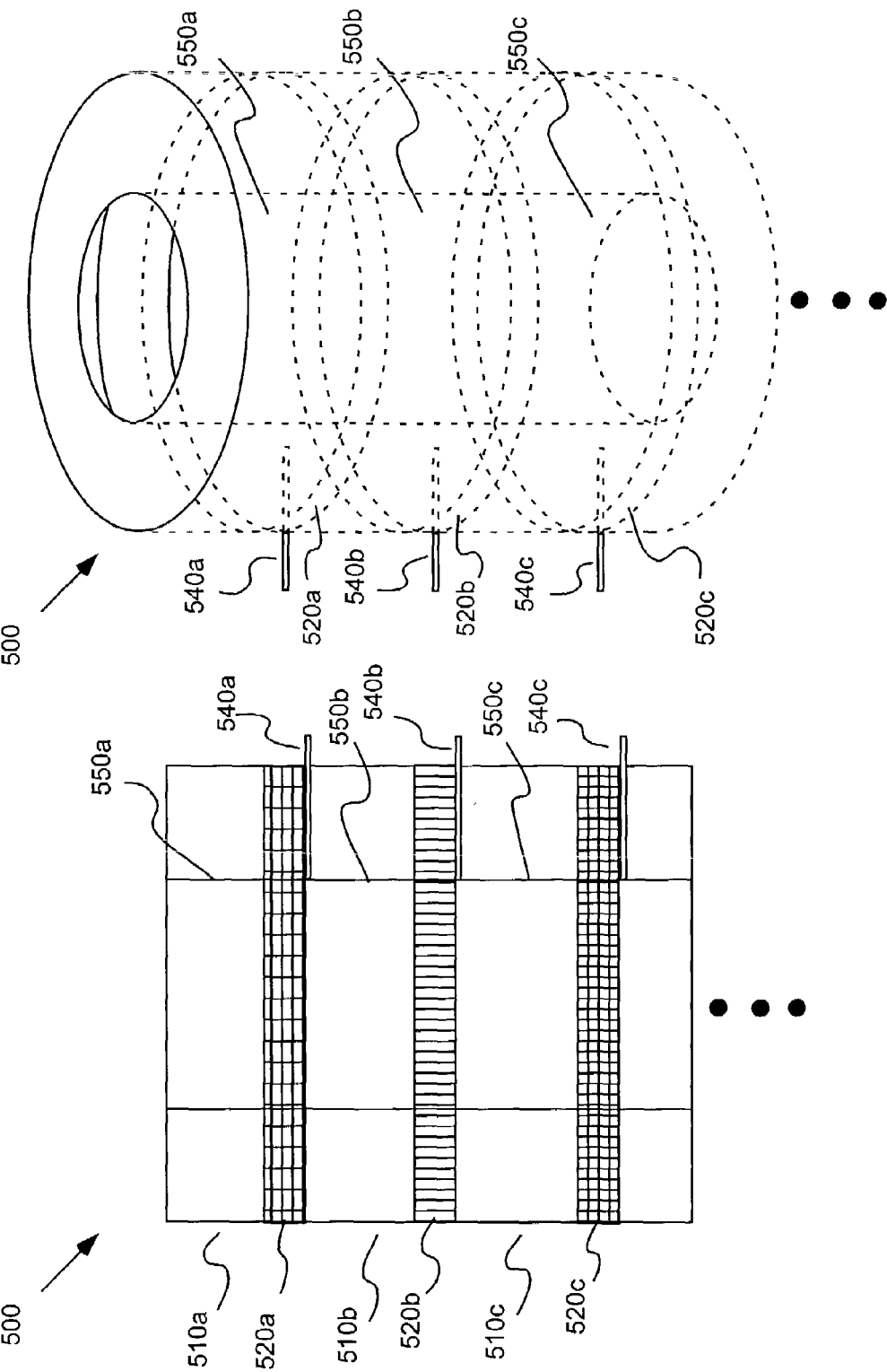

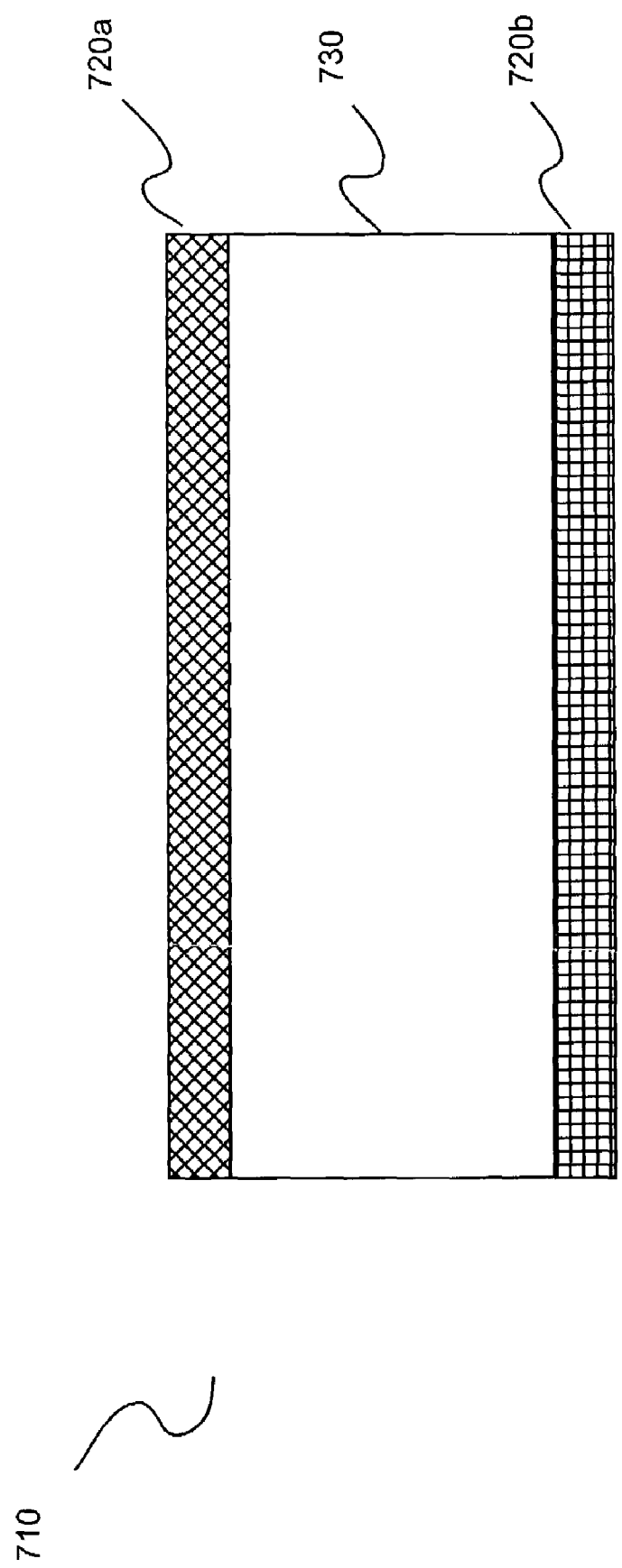

ELECTROCHEMICAL SENSOR

CROSS-REFERENCE TO RELATED APPLICATION

This application claims benefit of U.S. Provisional Patent Application 60/311,909 filed Aug. 13, 2001, the contents of which is incorporated herein by reference.

BACKGROUND OF THE INVENTION

The present invention relates to an electrochemical sensor, and particularly, to an electrochemical sensor having improved response time.

In a typical electrochemical gas sensor, the gas to be measured typically passes from the atmosphere into the sensor housing through a gas porous or gas permeable membrane to a working electrode (sometimes called a sensing electrode) where a chemical reaction occurs. A complementary chemical reaction occurs at a second electrode known as a counter electrode (or an auxiliary electrode). The electrochemical sensor produces an analytical signal via the generation of a current arising directly from the oxidation or reduction of the analyte gas (that is, the gas to be detected) at the working and counter electrodes. A comprehensive discussion of electrochemical gas sensors is also provided in Cao, Z. and Stetter, J. R., "The Properties and Applications of Amperometric Gas Sensors," *Electroanalysis,* 4 (3), 253 (1992), the disclosure of which is incorporated herein by reference.

To be useful as an electrochemical sensor, a working and counter electrode combination must be capable of producing an electrical signal that is (1) related to the concentration of the analyte and (2) sufficiently strong to provide a signal-to-noise ratio suitable to distinguish between concentration levels of the analyte over the entire range of interest. In other words, the current flow between the working electrode and the counter electrode must be measurably proportional to the concentration of the analyte gas over the concentration range of interest.

In addition to a working electrode and a counter electrode, an electrochemical sensor can include a third electrode, commonly referred to as a reference electrode. A reference electrode is used to maintain the working electrode at a known voltage or potential. The reference electrode should be physically and chemically stable in the electrolyte and carry the lowest possible current to maintain a constant potential.

Electrical connection between the working electrode and the counter electrode is maintained through an electrolyte. The primary functions of the electrolyte are: (1) to efficiently carry the ionic current; (2) to solubilize the analyte gas; (3) to support both the counter and the working electrode reactions; and (4) to form a stable reference potential with the reference electrode. The primary criteria for an electrolyte include the following: (1) electrochemical inertness; (2) ionic conductivity; (3) chemical inertness; (4) temperature stability; (5) low cost; (6) low toxicity; (7) low flammability; and (8) appropriate viscosity.

In general, the electrodes of an electrochemical cell provide a surface at which an oxidation or a reduction reaction occurs to provide a pathway whereby the ionic conduction of the electrolyte is coupled with the electron conduction of the electrode to provide a complete circuit for a current.

The measurable current arising from the cell reactions of the electrochemical cell is directly proportional to the rate of reaction. Preferably, therefore, a high reaction rate is maintained in the electrochemical cell. For this reason, the counter electrode and/or the working electrode of the electrochemical cell generally comprise an appropriate electrocatalyst on the surface thereof to enhance the reaction rate. If the reaction rate of either half cell reaction is impeded, resulting in a low exchange current density, the equilibrium current of the electrochemical cell may be changed or perturbed during measurement. Such change can result in undesirable side reactions and/or nonlinear behavior over the range of analyte concentrations desired to be detected.

The type, rate, and efficiency of the chemical reactions within an electrochemical gas sensor are controlled, in significant part, by the material(s) used to make the working electrode and counter electrode. Indeed, extensive research efforts are expended to develop improved working electrodes, counter electrodes and electrochemical systems generally. See Cao, supra.

As illustrated in FIG. 1, electrodes 110 in electrochemical gas sensors 100 typically include a hydrophobic catalyst layer 120 adhered to a micro-porous, hydrophobic membrane 130 such as a Gore-tex® membrane. Membrane 130 is porous to gases from the exterior of sensor 100 but is not porous to the electrolyte 140 contained within the interior of sensor 100. Catalyst layer 120 is three-dimensional and hydrophobic. Catalyst layer 120 thus resists ingress of electrolyte 140 into its internal structure, especially if a quasi-solid state electrolyte is used. However, to be detected, the analyte gas (represented by arrows in FIG. 1) must reach a point where catalyst 120 and electrolyte 140 are in very close proximity with one another. The gas must first diffuse through membrane 130, then into catalyst layer 120 and then through catalyst layer 120 until it reaches a catalyst/electrolyte interface 150. At interface 150, the gas is oxidized or reduced as described above. The time required for the gas to diffuse from the outside environment to such an interface 150 has a substantial effect upon the sensor response time.

It is desirable, therefore, to develop new electrochemical sensors and electrodes for use in such electrochemical sensors for the detection of analyte gases exhibiting improved response time.

SUMMARY OF THE INVENTION

In one aspect, the present invention provides an electrode for use in an electrochemical sensor including a catalyst dispersed within an electrolyte. Preferably, the catalyst is immobilized within a matrix of the electrolyte.

In current electrochemical sensors in which a liquid electrolyte is used, the liquid electrolyte can penetrate a solid catalyst layer formed on an electrode of the sensor to provide conductive contact. In a number of electrochemical sensors (for example, electrochemical sensors with metallic housings) it is desirable, however, to immobilize the electrolyte. In current sensors with immobilized electrolytes, there is generally no penetration of a catalyst layer of an electrode thereof by the immobilized electrolyte. Interfacial contact between the electrolyte and the catalyst can thus be diminished as compared to sensors in which a liquid electrolyte is used. The present inventors have discovered that good contact between a catalyst and an immobilized electrolyte can be achieved, while maintaining catalyst activity, by dispersing/immobilizing the catalyst within the electrolyte.

In one embodiment, the electrode of the present invention includes at least one catalyst/electrolyte layer having a mixture of a powdered catalyst, a powdered, quasi-solid electrolyte and a binder material compressed together. The quasi-solid electrolyte can include a liquid electrolyte immobilized by a high-surface-area, high-pore-volume solid. The solid can, for example, be $SiO_2$. The liquid electrolyte can, for example, be $H_2SO_4$. An example of a suitable binder material is polytetrafluoroethylene.

The electrode can further include at least one electrolyte layer adjacent to the catalyst/electrolyte layer. The electrolyte layer can include a mixture of a powdered, quasi-solid electrolyte and a binder material compressed together. The electrolyte layer can be bound to the catalyst/electrolyte layer. As described above, the quasi-solid electrolyte of the electrolyte layer can include a liquid electrolyte immobilized by a high-surface area, high-pore volume solid.

In another aspect, the present invention provides an electrochemical sensor for the detection of an analyte gas including a housing with at least one working electrode and at least one counter electrode disposed therein. The working electrode includes a catalyst dispersed within an electrolyte as described above. The catalyst is preferably immobilized within a matrix of the electrolyte.

In one embodiment, the working electrode includes at least one catalyst/electrolyte layer having a mixture of powdered catalyst, powdered, quasi-solid electrolyte and binder material compressed together as described above. The working electrode can further include at least one electrolyte layer adjacent to the catalyst/electrolyte layer. The electrolyte layer preferably includes a mixture of a powdered, quasi-solid electrolyte and a binder material compressed together.

The counter electrode can also include at least one catalyst/electrolyte layer having a mixture of powdered catalyst powdered, quasi-solid electrolyte and binder material compressed together. The catalysts of the working electrode and/or the counter electrode can, for example, independently be iridium, platinum, carbon, silver or gold. In one embodiment, the catalyst of the working electrode is iridium and the catalyst of the counter electrode is iridium. Such a sensor is, for example, operable to sense hydrogen sulfide.

The sensor can further include a reference electrode having at least one catalyst/electrolyte layer including a mixture of a powdered catalyst, a powdered, quasi-solid electrolyte and a binder material compressed together.

In still another aspect, the present invention provides a method of fabricating an electrode for use in an electrochemical sensor comprising the step of dispersing a catalyst within an electrolyte. The catalyst is preferably immobilized within a matrix of the electrolyte.

The step of dispersing a catalyst within an electrolyte can include the step of forming a catalyst/electrolyte layer by mixing a powdered catalyst, a powdered, quasi-solid electrolyte and a binder material and compressing the mixture. The method can further include the steps of: forming an electrolyte layer by mixing a powdered, quasi-solid electrolyte and a binder material; and compressing the mixture together. The step of compressing the mixture of a powdered, quasi-solid electrolyte and a binder material of the electrolyte layer can, for example, be done over the compressed mixture of powdered catalyst, powdered, quasi-solid electrolyte and binder material of the catalyst/electrolyte layer to form an electrolyte layer bound to the catalyst/ electrolyte layer.

The electrodes, sensors and methods of the present invention improve catalyst electrolyte contact and improve sensor response time as compared to sensors incorporating electrodes in which a hydrophobic catalyst layer is deposited upon a porous membrane. Moreover, the electrodes of the present invention are relatively easy and inexpensive to manufacture in various sizes and, particularly, in reduced size as compared to currently available electrodes. The reduced size of the electrodes of the present invention facilitate the manufacture of compact sensors. Additionally, the electrodes of the present invention are easily formed as, for example, stacks of multiple electrodes or multiple-layer electrodes for manufacture of compact sensors suitable for detection of multiple analytes. The electrodes of the present invention are also suitable for use with generally any electrolyte, including aqueous, inorganic and/or organic electrolytes. The electrolytes used with the electrodes of the present invention can also be acidic, basic or neutral. Still further, the electrodes of the present invention have been found to provide improved response signals, particularly with catalyst materials of intrinsically low surface area (for example, gold).

BRIEF DESCRIPTION OF THE DRAWINGS

FIG. 4A illustrates a side, cross sectional view of a portion of a sensor including a plurality of bi-layer electrodes of the present invention.

FIG. 4B illustrates a top perspective view of the sensor portion of FIG. 4A.

FIG. 5 illustrates an embodiment of a tri-layer composite electrode of the present invention.

DETAILED DESCRIPTION OF THE INVENTION

It is believed that the electrodes of the present invention improve response time of sensors incorporating the electrodes by making regions where catalyst and electrolyte form an interface favorable to reaction more available to the analyte gas. The electrodes of the present invention can be formed as multi-layer pellets. The pellet has at least one layer including a mixture of catalyst powder and a powdered quasi-solid state electrolyte. Mixing the catalyst and the electrolyte together results in intimate contact between the catalyst and the electrolyte. The relatively thick, hydrophobic catalyst layer characteristic of currently available electrodes is eliminated. The analyte gas has direct access to catalyst/electrolyte interfaces immediately, for example, after passing through a membrane, resulting in faster response times.

Figure 1:
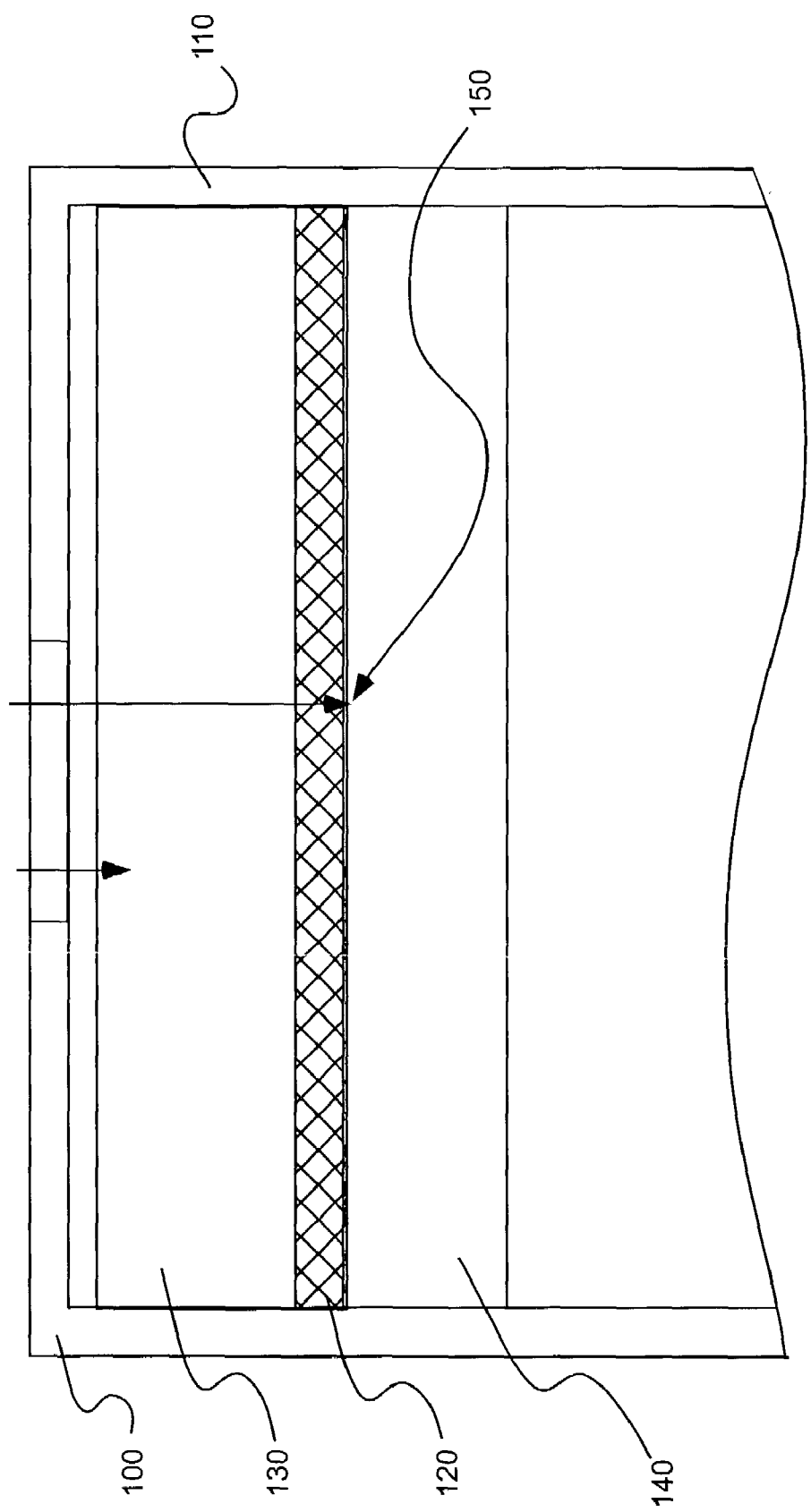
FIG. 1 illustrates a side cross-sectional view of a portion of a sensor incorporating an electrode in which a catalyst is deposited upon a porous membrane.
Figure 2A:
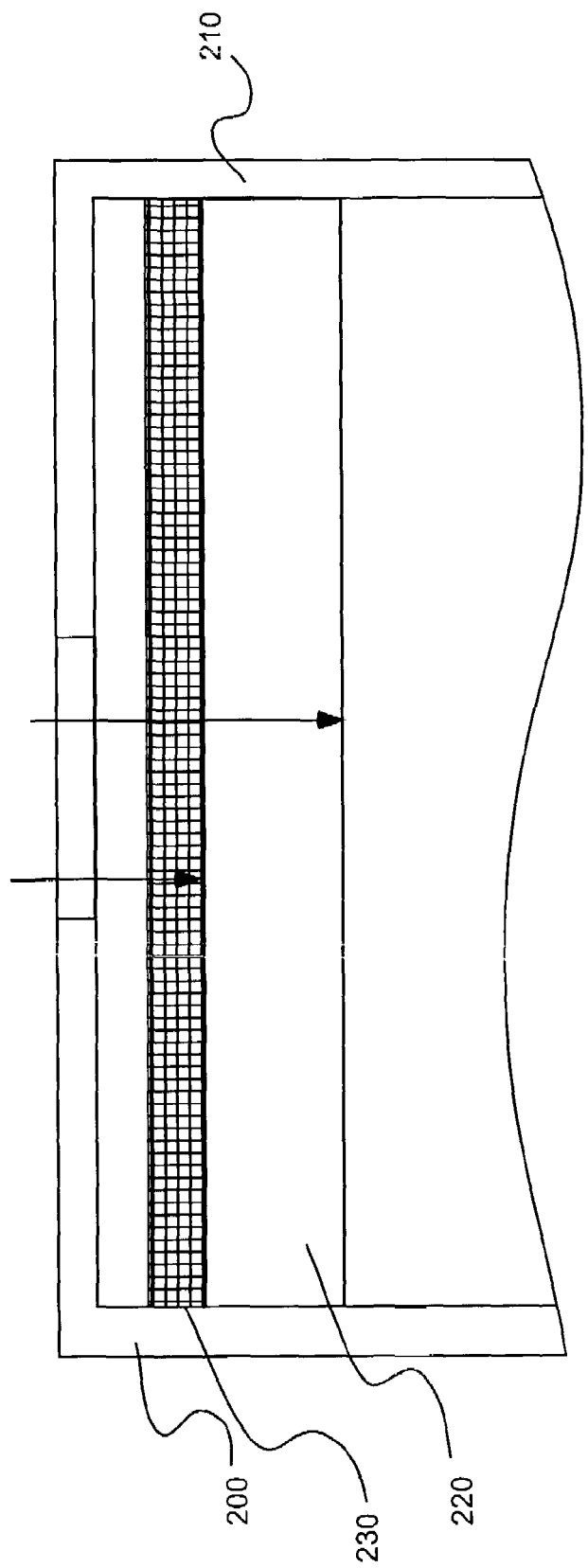
FIG. 2A illustrates a side cross-sectional view of a sensor incorporating a bi-layer, composite electrode of the present invention.
Figure 2B:
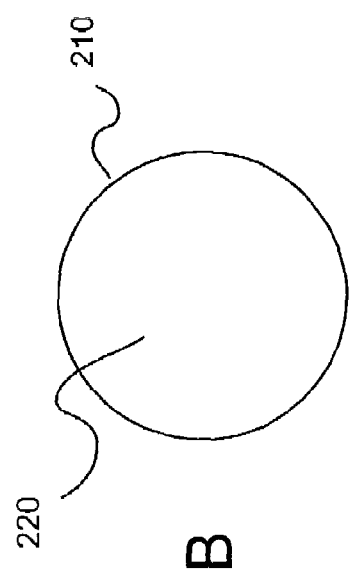
FIG. 2B illustrates a top plan view of the electrode of FIG. 2A.

FIGS. 2A and 2B illustrate a bi-layer pellet electrode 210 of the present invention in a sensor 200. As illustrated in FIG. 2B, bi-layer pellet electrode 210 is of generally circular shape. Bi-layer pellet electrode 210 includes an electrolyte layer 220 and a catalyst/electrolyte layer 230. Electrolyte layer 220 is made from a composite powder containing a mixture an electrolyte material, a powder having a relatively high surface area and a relatively high pore volume and a binder material. In general, the powder is a porous powder such as a porous ceramic or a porous polymer.

Binder materials used in the present invention can be polymeric materials that are suitable to form a three-dimensional matrix around and thus bind together the electrolyte material. The binder material is preferably generally inert to the electrolyte material, to the catalyst and to substances to which the sensor will be exposed during use. An example of a suitable binder material is a polymer such as TEFLON (polyfluorotetraethylene or PTFE) and like materials that are generally inert and have glass transitions temperature above which the polymer softens and can flow (for example, during pressing) to form a three-dimensional matrix or support, binding the electrolyte material together. A binder material for use in the present invention can also be a powder having a particle size different from the particle size of the electrolyte material that is suitable to form an interlocking matrix with the electrolyte material.

In several electrodes studied in the present invention, the electrolyte was $H_2SO_4$, the high-surface-area, high-pore-volume powder was $SiO_2$ and the binder was PTFE (TEFLON). An example of a suitable $SiO_2$ powder is SIPERNAT® 22 (a synthetic amorphous precipitated silica powder) available from Degussa AG of Frankfurt, Germany. That silica powder was indicated by the manufacturer to have a BET surface area of approximately 190 $m^2/g$. Catalyst/electrolyte layer 230 was made from the same mixture of materials used in the electrolyte layer 220 with the addition of an appropriate catalyst powder.

In several studies of the present invention, electrolyte layer 220 was first made by compressing a volumetrically measured sample of the above-described mixture in a die cavity. A second volumetrically measured sample of catalyst/electrolyte layer mixture is then pressed on top of electrolyte layer 220 to produce one, bi-layer pellet electrode 210. Of course, the order of formation of the layers can be reversed.

To produce a two-electrode sensor, two bi-layer pellets 210 can, for example, be placed back to back in the sensor assembly with their electrolyte layers 220 touching. This assembly provides ionic contact for sensor operation. The bi-layer pellet that is placed closest to the inlet hole in the sensor can function as the sensing (working) electrode. The bi-layer pellet that is placed farthest away from the inlet hole can function as the counter/reference electrode. Selectivity for a specific target gas is obtained by choosing the appropriate catalyst combination for the sensing pellet electrode and the counter/reference pellet electrode. Three-electrode sensors can be made by adding an additional bi-layer pellet electrode to serve exclusively as a reference electrode, as opposed to a counter/reference electrode. The reference pellet electrode can, for example, be placed between the sensing and counter pellet electrodes.

Figures 3A, 3B:
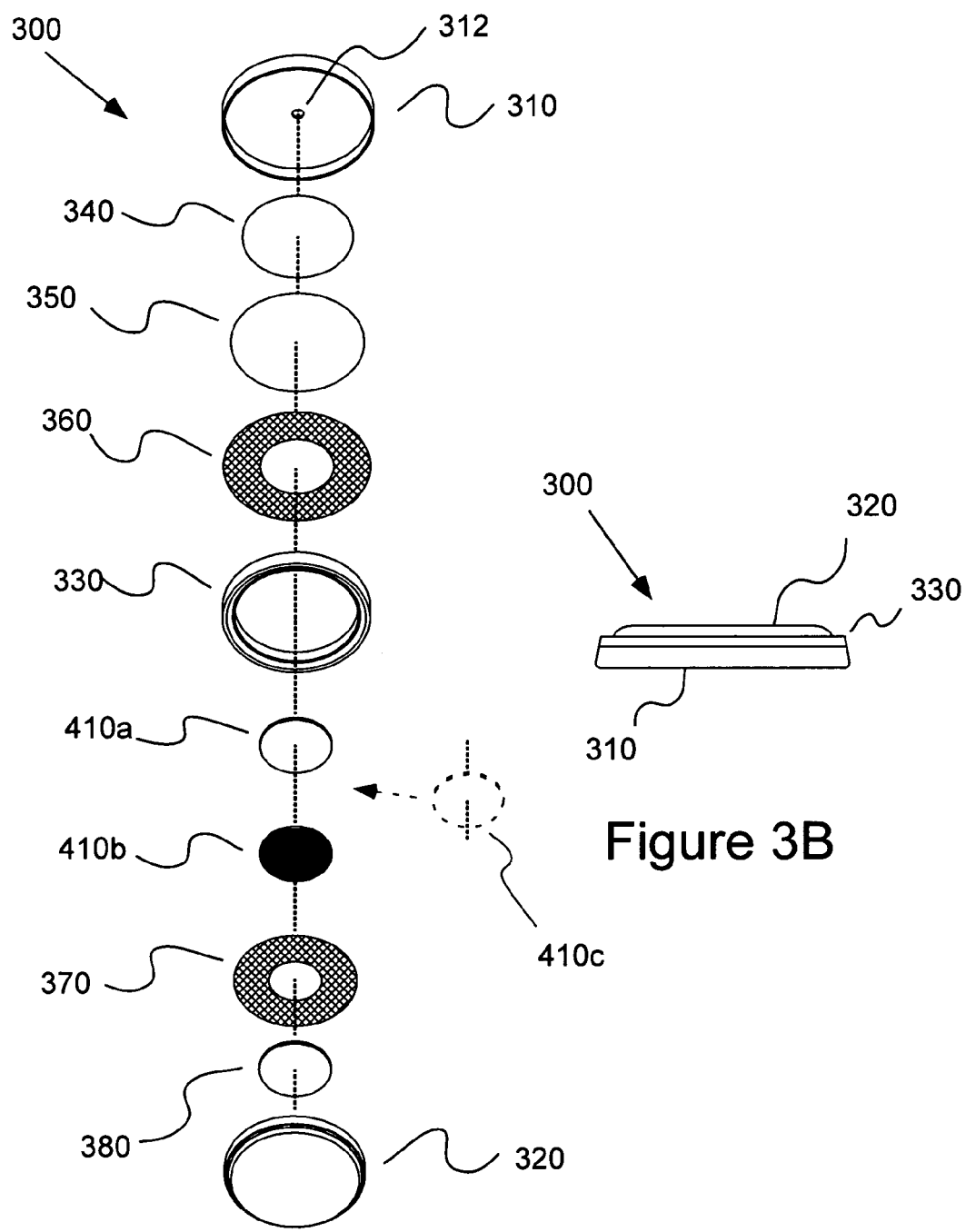
FIG. 3A illustrates a disassembled or exploded view of a two-electrode sensor including two bi-layer electrodes of the present invention.
FIG. 3B illustrates a side view of the sensor of FIG. 3A in an assembled state.

FIGS. 3A and 3B illustrate an assembly of one embodiment of a two-electrode sensor 300 of the present invention. Sensor 300 is housed within a metallic cell or case as described, for example, in U.S. Pat. Nos. 5,906,726 and 5,667,653, the contents of which are incorporated herein by reference. In that regard, sensor 300 includes a first case member 310 in which an inlet 312 is formed to allow analyte gas to enter sensor 300 from the surrounding environment. Sensor 300 also includes a second case member 320 which can be crimped under first case member 310 to form the outer housing of sensor 300 as illustrated in FIG. 3B.

A gasket 330 can be placed within sensor 300 to assist in forming an adequate connection/seal between case members 310 and 320, to provide electrical insulation between case members 310 and 320, and to assist in positioning the other components of sensor 300 within the sensor housing. One or more filters 340 and 350 can be placed adjacent first case member 310 within sensor 300. Filter 340 can, for example, be a spun mat glass filter suitable, for example, to diffuse gas entering sensor 300 and/or to remove interferants. Filter 350 can, for example, be a porous GORE-TEX® membrane available from W. L. Gore & Associates and suitable to filter solids and liquids, but porous to gases. In the embodiment of FIGS. 3A and 3B, a screen contact member 360 is placed in electrical contact with the electrolyte/catalyst layer of bi-layer pellet working electrode 410a and with first case member 310. A second screen contact member 370 is placed in electrical contact with the electrolyte/catalyst layer of bi-layer pellet counter electrode 410b and with second case member 320. A buffer or spacer 380 is placed between pellet counter electrode 410b and second case member 320. A reference electrode 410c can be added to form a three-electrode sensor as described in U.S. Pat. Nos. 5,906,726 and 5,667,653.

As illustrated in FIGS. 4A and 4B, several pellet electrodes 510a, 510b, 510c ••• can be incorporated into a sensor 500 for the detection of multiple analyte gases. Each of bi-layer pellet electrodes 510a, 510b, 510c ••• can, for example, be fabricated as described above. However, each of electrolyte/catalyst layers 520a, 520b, 520c ••• can include a different catalyst (for example, platinum (Pt), iridium (Ir), gold (Au) etc.) as desired to catalyze a reaction of and thereby sense the presence of different analyte gases. Electrical contact members 540a, 540b, 540c ••• are placed in contact with electrolyte/catalyst layers 520a, 520b, 520c ••• to carry a signal to, for example, a measurement circuit as known in the art. In the embodiment of FIGS. 4A and 4B, electrodes 510a, 510b, 510c ••• are, for example, formed in the shape of a cylindrical rings with passages 550a, 550b, 550c •••formed generally centrally therein. Passages 550a, 550b, 550c ••• form a composite passage generally through the center of sensor 500 when electrodes 510a, 510b; 511c ••• are stacked in general alignment through which analyte gasses can pass to contact catalyst/electrolyte layers 520a, 520b, 520c •••.

Figure 4C:
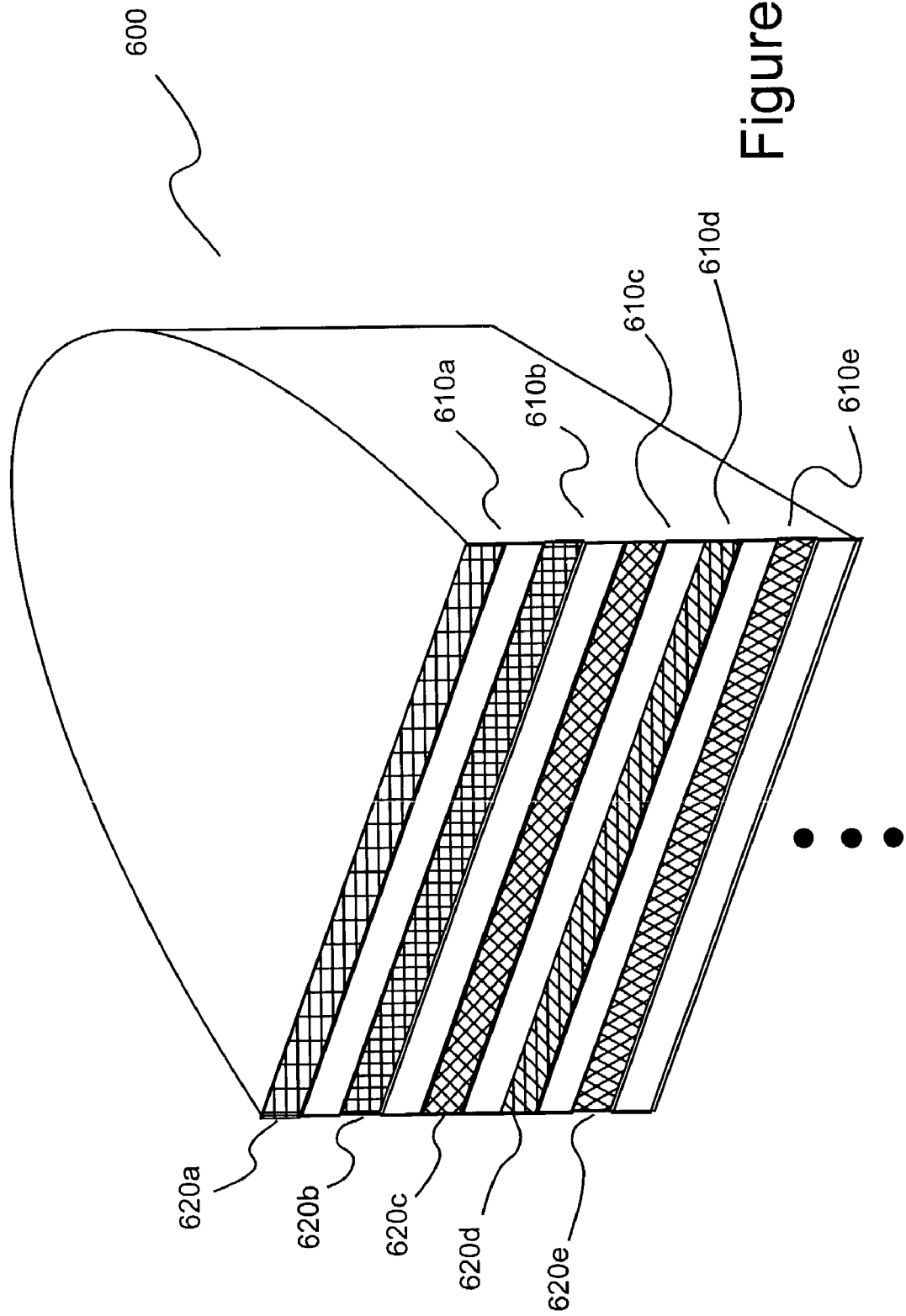
FIG. 4C illustrates a top perspective view of another sensor including a plurality of bi-layer electrodes of the present invention.

FIG. 4C illustrates another embodiment of a sensor 600 in which several pellet electrodes 610a, 610b, 610c, 610d, 610e ••• can be incorporated into a sensor 600 for the detection of multiple analyte gases. Each of bi-layer pellet electrodes 610a, 610b, 610c, 610d, 610e ••• can, for example, be fabricated as described above. Each of electrolyte/catalyst layers 620a, 620b, 620c, 620d, 620e ••• can include a different catalyst as described above. In the embodiment of FIG. 4C, sensor 600 can be formed by first forming a generally circular or generally oval composite sensor, which is subsequently sliced/bisected to form two generally semicircular sensors 600 in which electrodes 610a, 610b, 610c, 610d, 610e ••• are stacked in general alignment and wherein analyte gasses can contact catalyst/electrolyte layers 620a, 620b, 620c, 620d, 620e ••• at the open face of electrode 600 created during bisection.

Moreover, the electrodes of the present invention can also be formed as multi-layer pellets other than bi-layer electrode. For example, FIG. 5 illustrates a tri-layer pellet electrode 710 including a first electrolyte/catalyst layer 720a, an intermediate electrolyte layer 730 and a second electrolyte/catalyst layer 720b. The catalysts of first electrolyte/catalyst layer 720a and second electrolyte/catalyst layer 720b can be different. Electrolyte/catalyst layers 720a and 720b, electrolyte layer 730 and any other electrolyte or electrolyte/catalyst layers can be formed generally as described above.

EXPERIMENTAL EXAMPLES

A number of electrodes as illustrated in FIGS. 3A and 3B were tested for various analyte gases using various electrode catalysts in a two-electrode sensor configuration as summarized in Table 1. The catalysts used in the studies of the present invention are further characterized in Table 2.

TABLE 1

| Analyte Gas | Active Catalyst Working Electrode | Active Catalyst Counter Electrode | Bias Potential |
|---|---|---|---|
| $H_2S$ | Iridium | Iridium | 0 mV |
| CO | Platinum | Platinum | 0 mV |
| $NO_2$ | Activated Carbon | Activated Carbon | 0 mV |
| $SO_2$ | Gold | Platinum | 0 mV |
| NO | Carbon | Platinum | +300 mV |
| $NH_3$ | Iridium | Iridium | +235 mV |

TABLE 2

| Catalyst | Manufacturer | Surface Area, $m^2/g$ | Sensor |
|---|---|---|---|
| Iridium | Englehard | 15.5–21.5 | $H_2S$ |
| Platinum | Englehard | >25 | CO, $SO_2$, NO |
| Activated Carbon | Johnson Matthey | Not Available | $NO_2$ (75%) |
| Carbon Black (Regal 330R) | Cabot | 94 | $NO_2$ (25%) |
| Gold | Technic Inc. | 0.4–1.0 | $SO_2$ |
| Graphite (EG-31) | Sigri Great Lakes Carbon Co. | Not Available | NO |

Each of the sensors studied included a working and counter electrode as described above. In forming the bi-layer electrodes, the electrolyte was $H_2SO_4$, the high-surface-area, high-pore-volume powder was $SiO_2$ and the binder was PTFE (TEFLON). As set forth in Table 1, in the case of $H_2S$ (hydrogen sulfide), CO (carbon monoxide) and $NO_2$ (nitrogen dioxide) analyte gases, the catalyst on the working and counter electrodes was the same. In the case of $SO_2$ (sulfur dioxide) and NO (nitric oxide) analyte gases, the catalyst on the working and counter electrodes was different. The NO sensor was operated at a positive bias potential (approximately +300 mV), whereas the other sensors were operated at a zero bias potential.

Studies were also performed upon NO sensors having a three-electrode configuration (working electrode, counter electrode and reference electrode). As with the two-electrode NO sensors, the three-electrode NO sensors were operated at a positive bias potential of approximately +300 mV.

In general, the present studies were performed under computer control in which twenty (20) sensors could be tested simultaneously. A baseline current reading for each sensor was established as the sensor output after an exposure to air (0 ppm analyte gas). In testing for analyte gas concentration, air was first applied to the sensors for a period of time followed by application of air having a known concentration of analyte gas for a period of time. A purge with air followed exposure to analyte gas in some experiments.

In general, the response time of the sensors of the present invention are substantially improved as compared to sensors in which currently available electrodes are used. Response time is a measure of the speed of response of a sensor and can be dependent on the manner in which the test is performed (for example, the length of time the experiment lasts and/or the time at which the sensor reaches 100% of its final output). In the present studies, response times were based on exposure to test gas for a known amount of time. Response time was generally tabulated as the 90% response time ($t_{90}$) unless otherwise indicated. The $t_{90}$ response time is the time, in seconds, required for the sensor to reach 90% of a generally stable response or output. The sensitivity (in units of μA/ppm analyte) was established as the sensor output after exposure to analyte gas for a sufficient period of time to reach a stable output.

Hydrogen Sulfide Sensors

Figure 6:
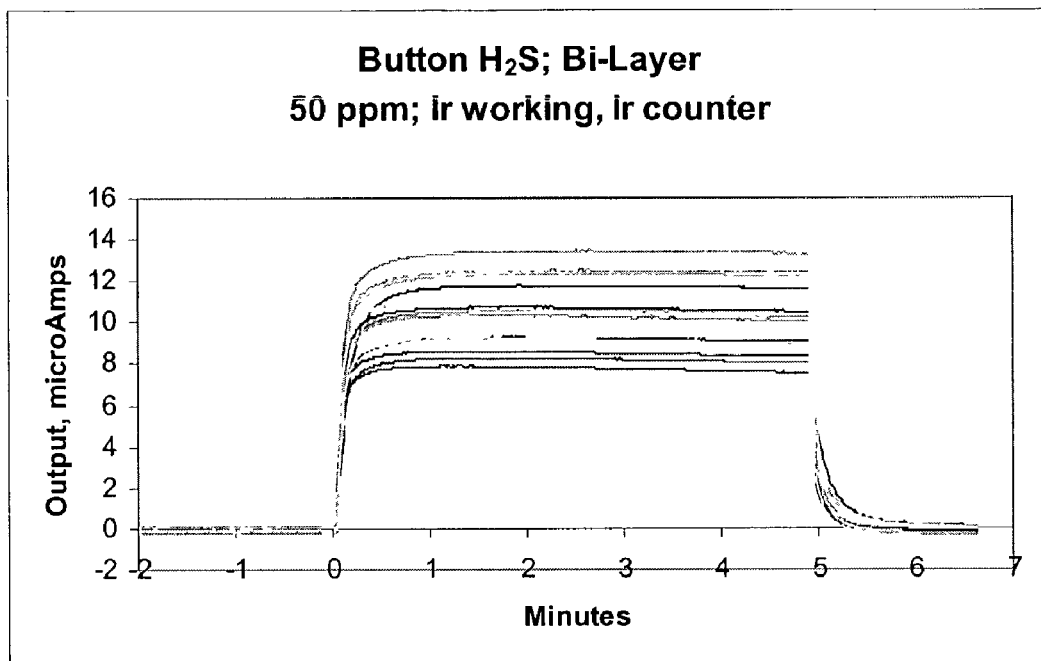
FIG. 6 illustrates a graph of the output of several two-electrode $H_2S$ sensors of the present invention.

As described in Table 1, $H_2S$ sensors of the present invention included a bi-layer working electrode having an iridium catalyst and a bi-layer counter electrode having an iridium catalyst. The electrodes and the sensors were formed generally as described above in connection with FIGS. 2A through 3B and as further described below. FIG. 6 illustrates the measured output for several such sensors over time during operation with a potentiostat at 0 mV bias potential. The experiments of FIG. 6 included 2 minutes of baseline in which the sensor was exposed to air without analyte gas, followed by 5 minutes of analyte gas exposure (50 ppm $H_2S$), followed by 2 minutes of air purge.

Table 2 summarizes results for 200 sensors using bi-layer electrodes of the present invention and 200 sensors using currently available electrodes in which catalyst is deposited upon a porous membrane. Errors reported in Table 3 represent one standard deviation.

TABLE 3

| Electrode Type | Sensitivity (Microamps/ppm) | Response Time, $T_{90}$ (Seconds) |
|---|---|---|
| Catalyst deposited on membrane | 0.194 ± 0.023 | 149 ± 36 |
| Bi-layer composite electrode | 0.189 ± 0.034 | 15 ± 4 |

Carbon Monoxide Sensors

Figure 7:
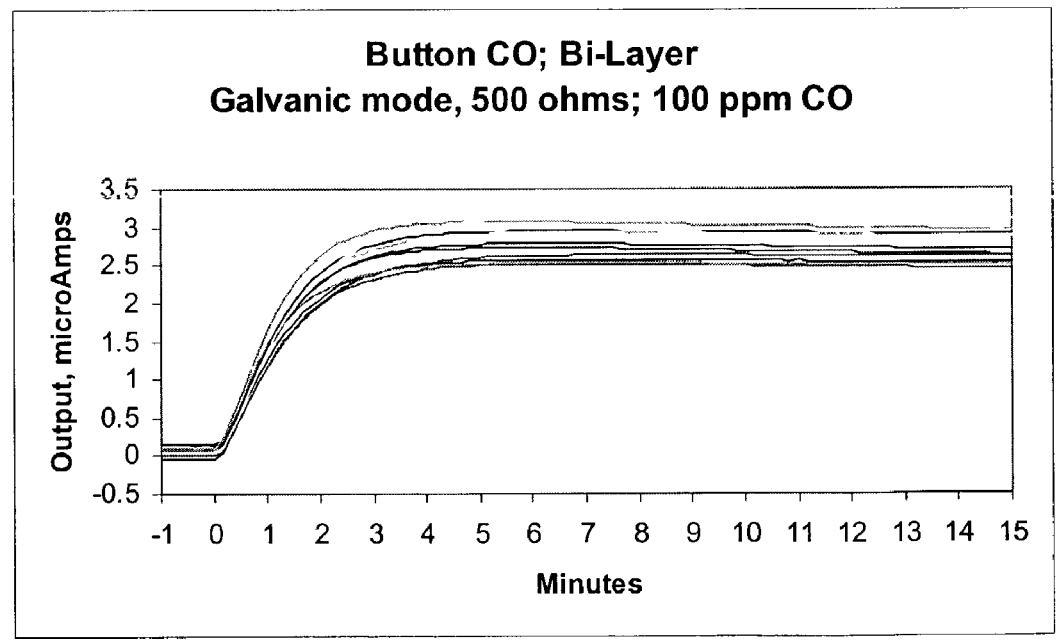
FIG. 7 illustrates a graph of the output of several two-electrode CO sensors of the present invention.

As described in Table 1, CO sensors of the present invention included a bi-layer working electrode having an platinum catalyst and a bi-layer counter electrode having an platinum catalyst. The electrodes and the sensors were formed generally as described above in connection with FIGS. 2A through 3B. FIG. 7 illustrates the measured output for several such sensors over time during galvanic operation using a 500 ohm resistor. The experiments of FIG. 7 included 1 minute of baseline in which the sensor was exposed to air without analyte gas (100 ppm CO), followed by 15 minutes of analyte gas exposure.

Nitrogen Dioxide Sensors

Figure 8:
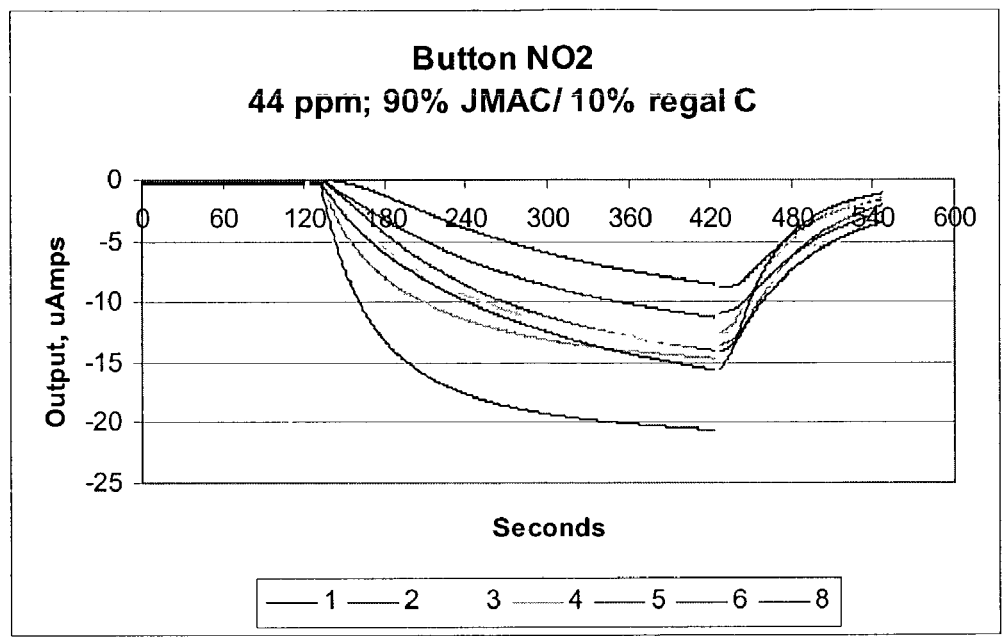
FIG. 8 illustrates a graph of the output of several two-electrode $NO_2$ sensors of the present invention.

As described in Table 1, $NO_2$ sensors of the present invention included a bi-layer working electrode having an activated carbon catalyst and a bi-layer counter electrode having an activated carbon catalyst. The activated carbon in each electrode was 75% activated carbon and 25% carbon black. The electrodes and the sensors were formed generally as described above in connection with FIGS. 2A through 3B. FIG. 8 illustrates the measured output for several such sensors over time during operation with a potentiostat at 0 mV bias potential. The experiments of FIG. 8 included 2 minutes of baseline in which the sensor was exposed to air without analyte gas, followed by 10 minutes of analyte gas exposure (44 ppm $NO_2$), followed by 2 minutes of air purge.

Sulfur Dioxide Sensors

Figure 9:
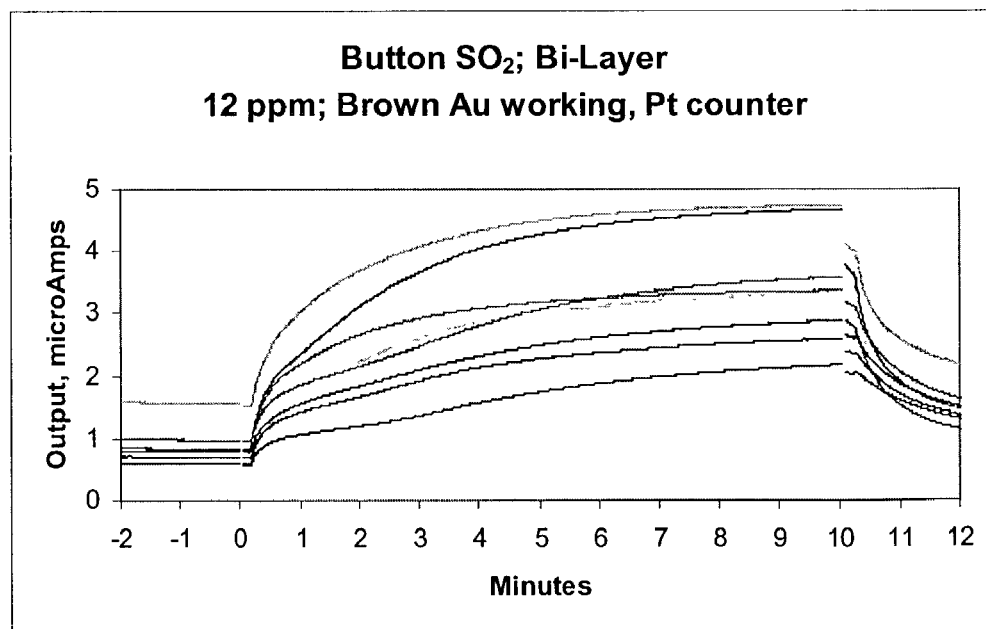
FIG. 9 illustrates a graph of the output of several two-electrode $SO_2$ sensors of the present invention.

As described in Table 1, $SO_2$ sensors of the present invention included a bi-layer working electrode having a gold catalyst and a bi-layer counter electrode having a platinum catalyst. The electrodes and the sensors were formed generally as described above in connection with FIGS. 2A through 3B FIG. 9 illustrates the measured output for several such sensors over time during operation with a potentiostat at 0 mV bias potential. The experiments of FIG. 9 included 2 minutes of baseline in which the sensor was exposed to air without analyte gas, followed by 10 minutes of analyte gas exposure (12 ppm $SO_2$), followed by 2 minutes of air purge.

Nitric Oxide Sensors (Two Electrode Configuration)

Figure 10:
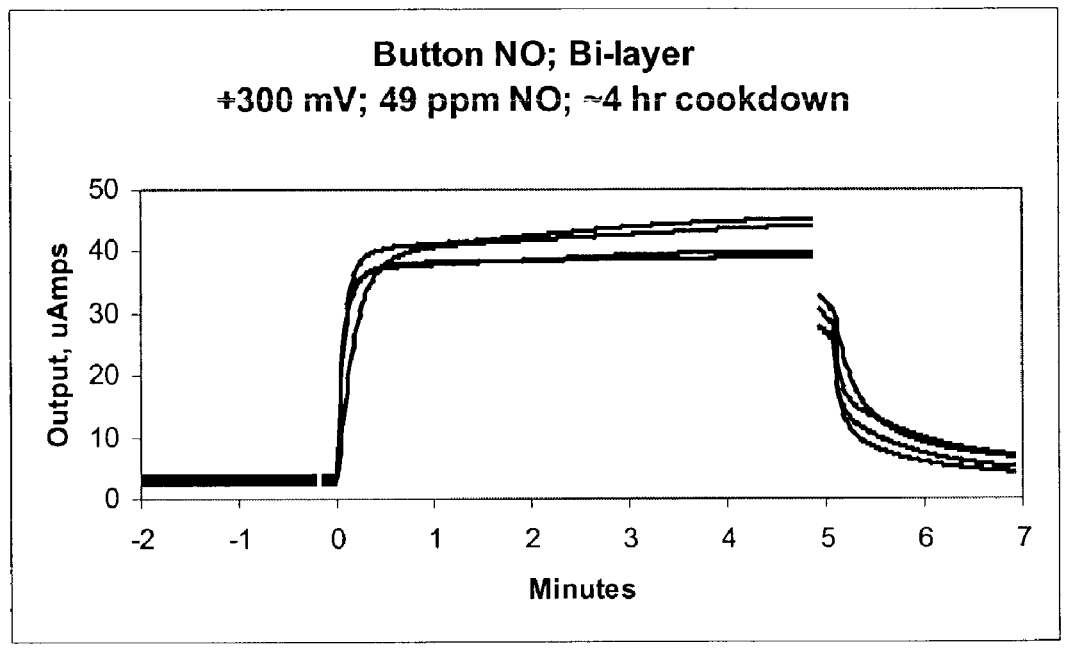
FIG. 10 illustrates a graph of the output of several two-electrode NO sensors of the present invention.

As described in Table 1, NO sensors of the present invention included bi-layer working electrode having a carbon catalyst and a bi-layer counter electrode having a platinum catalyst. The electrodes and the sensors were formed generally as described above in connection with FIGS. 2A through 3B. FIG. 10 illustrates the measured output for several such sensors over time during operation with a potentiostat at +300 mV bias potential. The of FIG. 9 included 2 minutes of baseline in which the sensor was exposed to analyte gas, followed by 5 minutes of analyte gas exposure (49 ppm NO), followed 2 minutes of air purge. Data including response times for several NO sensors are also set forth in Table 4.

TABLE 4

| Sensor | Base Current (uAmps) | Output Response (uA/PPM) | Response Time (Secs) |
|---|---|---|---|
| 1 | 3.326 | 0.870 | 45 |
| 2 | 2.338 | 0.763 | 14 |
| 3 | 3.920 | 0.836 | 45 |
| 4 | 2.360 | 0.781 | 17 |

Often, electrochemical sensors are subjected to a "cook-down" or "equilibration" period before use thereof to provide an adequately stable and low baseline current. During the cook-down or equilibration period, the electrochemical sensor is stored at ambient conditions and maintained at operating potential for a defined period of time. A cook-down period of approximately 4 hours was used in the studies of FIG. 9 and Table 4.

Nitric Oxide Sensors (Three Electrode Configuration)

Figure 11:
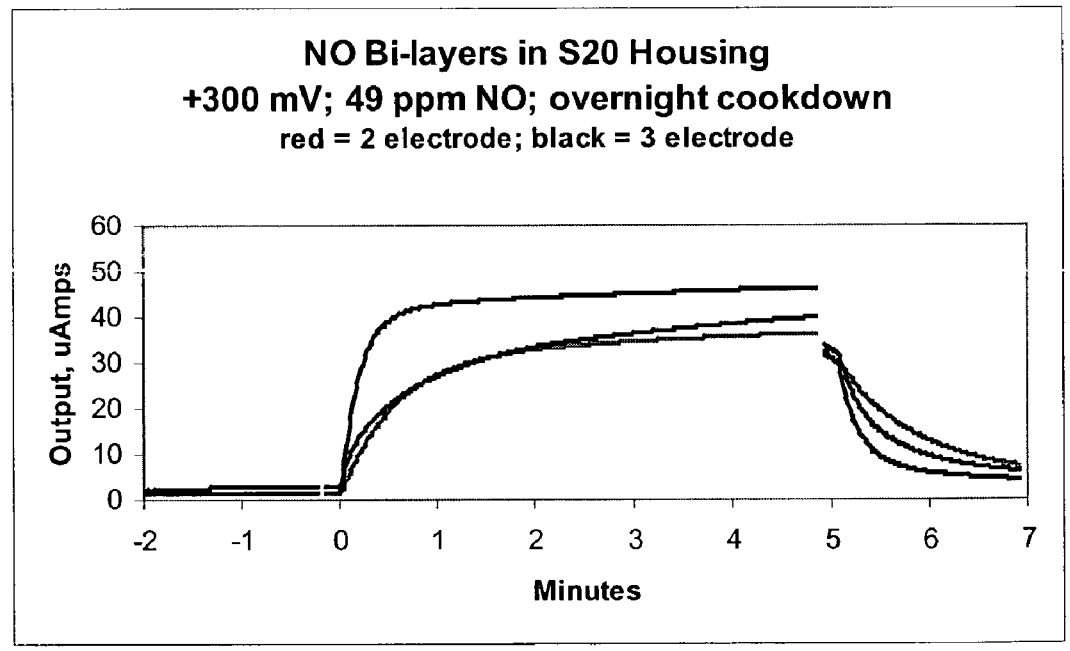
FIG. 11 illustrates a graph of a comparison of the output of a two-electrode NO sensor of the present invention and two three-electrode NO sensors of the present invention.

Three-electrode NO sensors of the present invention included a bi-layer working electrode having a carbon catalyst, a bi-layer counter electrode having a platinum catalyst and a bi-layer reference electrode having a platinum catalyst. The electrodes and the sensors were formed generally as described above in connection with FIGS. 2A through 3B. However, a reference electrode was included in sensor 2 and 3 of FIG. 11 and Table 5. The three-electrode sensor was prepared generally in the manner described in U.S. Pat. Nos. 5,906,726 and 5,667,653. Sensor 1 included only a working and a counter electrode as described above. FIG. 11 illustrates the measured output for several such sensors over time during operation with a potentiostat at +300 mV bias potential. The experiments of FIG. 11 included 2 minutes of baseline in which the sensor was exposed to air without analyte gas, followed by 5 minutes of analyte gas exposure (49 ppm NO), followed by 2 minutes of air purge. An overnight cook-down period was use in the studies. Data including response times for the two-electrode NO sensor and the two three-electrode NO sensors are set forth in Table 5.

TABLE 5

| Sensor | Base Current (uAmps) | Output Response (uA/PPM) | Response Time (Secs) |
|---|---|---|---|
| 1 | 1.528 | 0.709 | 113 |
| 2 | 3.013 | 0.754 | 172 |
| 3 | 1.450 | 0.918 | 45 |

Ammonia Sensors (Neutral or Basic Electrolyte)

Ammonia sensors were fabricated similarly to other bi-layer sensors described above. The electrolyte used was 5 M LiCl solution, absorbed onto an $SiO_2$ support in a 0.75:1 weight ratio ($LiCl:SiO_2$). The catalyst was Ir powder. The electrodes and the sensors were formed generally as described above in connection with FIGS. 2A through 3B. The ammonia sensors were operated in the electrolytic mode at approximately +235 mV in sensing ammonia gas.

Preparation of Electrolyte Powder

In preparation of typical preparation, approximately 190 grams of precipitated silica (DeGussa SIPERNAT 22) was placed into a round, ½ gal. Nalgene mixing container under a ventilated hood. Approximately 165 grams of PTFE powder (Dupont Teflon 850A) was then added to the mixing container. The mixing container was then closed and lightly shaken to pre-mix the components.

Approximately 145 grams of 6.7N sulfuric acid was then poured into the pre-mixed powder. The cap was then closed and the container gently shaken for a few seconds to disperse the liquid. The mixing container was then tumbled for 15–20 minutes at approximately 40 rpm using a LorTone rock tumbler.

Preparation of Electrolyte/Catalyst Powder

In a typical case of an iridium catalyst as described above, each pellet of a sensor included approximately 0.06 grams of electrolyte/catalyst powder per pellet. The electrolyte/catalyst powder was approximately 50% electrolyte powder as described above and approximately 50% catalyst blend powder as described below.

In one example, 2.4 grams PTFE (DuPont Teflon 850A), 0.8 grams graphite, 0.8 grams precipitated silica (DeGussa SIPERNAT were added to a mixing container. After addition of these components, the container was lightly shaken for about 5 minutes. Then the electrolyte powder was added. Approximately, 8 grams of Iridium powder were added to the mixing container. The mixing container was then place in a rubber sleeve and tumbled using a LorTone rock tumbler for about 15 minutes at approximately 40 rpm.

Preparation of Pellets

In forming a bilayer pellet, the cavity of a die having a fill depth of approximately 0.117 inches and a diameter of approximately 0.5 in. was first filled with electrolyte powder as described above flush with the top of the die. A metal rod was used to gently tamp the powder down. A first stop was then slid over the die; causing a small depression. This depression defined the fill depth for the electrolyte/catalyst powder as describe above. The resulting cavity or depression was then filled with a small amount of catalyst/electrolyte powder. Excess powder was scraped off so that the powder was flush with the top of the die. The top platen was place on the top of the cavity, and the die was slid under a ram. The pellet was then pressed with a dwell time at the bottom of the stroke of approximately 3–5 seconds. The ram was in operative connection to a 6 inch air cylinder to which compressed air was supplied at a pressure of approximately 90 to approximately 110 psi. After retraction of the die, the pellet was removed. In general, the bilayer pellet electrodes used in the studies of the present invention had a thickness in the range of approximately 0.044 to approximately 0.047 inches. The electrolyte layer of the bilayer pellet electrodes was in the range of approximately 0.037 to approximately 0.040 inches thick.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An electrode for use in an electrochemical sensor comprising: at least one catalyst/electrolyte layer comprising a mixture of a powdered catalyst and a powdered, quasi-solid electrolyte comprising a liquid electrolyte immobilized by a high-surface-area, high-pore-volume solid compressed together, and at least one electrolyte layer adjacent to the catalyst/electrolyte layer, the electrolyte layer including a mixture of a powdered, quasi-solid electrolyte comprising a liquid electrolyte immobilized by a high-surface-area, high-pore-volume solid and a binder material compressed together.

2. The electrode of claim 1 wherein the electrode further comprises a binder material compressed together with the powdered catalyst and the powdered catalyst of the catalyst/electrolyte layer.

3. The electrode of claim 2 wherein the binder material of the catalyst/electrolyte layer is polytetrafluoroethylene.

4. The electrode of claim 1 wherein the solid of catalyst/electrolyte layer is $SiO_2$.

5. The electrode of claim 4 wherein the liquid electrolyte is $H_2SO_4$.

6. The electrode of claim 1 wherein the electrolyte layer is bound to the catalyst/electrolyte layer.

7. The electrode of claim 6 wherein the catalyst comprises iridium, platinum, carbon, silver or gold.

8. The electrode of claim 6 wherein the binder material of the electrolyte layer is polytetrafluoroethylene.

9. The electrode of claim 1 wherein the solid of the electrolyte layer is $SiO_2$.

10. The electrode of claim 9 wherein the liquid electrolyte of the electrolyte layer is $H_2SO_4$.

11. An electrochemical sensor for the detection of an analyte gas comprising; a housing, the housing having disposed therein at least one working electrode and at least one counter electrode, the mixture of a powdered catalyst and a powdered, quasi-solid electrolyte comprising a liquid electrolyte immobilized by a high-surface-area, high-pore-volume solid, and at least one electrolyte layer adjacent to the catalyst/electrolyte layer, the electrolyte layer including a mixture of a powdered, quasi-solid electrolyte comprising a liquid electrolyte immobilized by a high-surface-area, high-pore-volume solid and a binder material compressed together.

12. The sensor of claim 11 wherein the electrode further comprises a binder material compressed together with the powdered catalyst and the powdered catalyst of the catalyst/electrolyte layer of the working electrode.

13. The sensor of claim 12 wherein the solid is $SiO_2$.

14. The sensor of claim 13 wherein the liquid electrolyte of the catalyst/electrolyte layer or the working electrode is $H_2SO_4$.

15. The sensor of claim 12 wherein the binder material is polytetrafluoroethylene.

16. The sensor of claim 11 wherein the electrolyte layer is bound to the catalyst/electrolyte layer.

17. The sensor of claim 11 wherein the catalyst comprises iridium, platinum, carbon, silver or gold.

18. The sensor of claim 11 wherein the solid of the electrolyte layer is $SiO_2$.

19. The sensor of claim 18 wherein the liquid electrolyte of the electrolyte layer is $H_2SO_4$.

20. The sensor of claim 19 wherein the binder material of the electrolyte layer is polytetrafluoroethylene.

21. The sensor of claim 20 wherein the catalyst of the working electrode includes iridium, platinum, carbon, silver or gold.

22. The sensor of claim 21 wherein the counter electrode includes at least one catalyst/electrolyte layer having a mixture of powdered catalyst, powdered, quasi-solid electrolyte comprising a liquid electrolyte immobilized by a high-surface-area, high-pore-volume solid and binder material compressed together.

23. The sensor of claim 22 wherein the catalyst of the counter electrode includes iridium, platinum, carbon, silver or gold.

24. The sensor of claim 23 wherein the catalyst of the working electrode is iridium and the catalyst of the counter electrode is iridium, the sensor being operable to sense hydrogen sulfide.

25. The sensor of claim 22 further including a reference electrode having at least one catalyst/electrolyte layer including a mixture of a powdered catalyst, a powdered, quasi-solid electrolyte and a binder material compressed together.

26. A method of fabricating an electrode for use in an electrochemical sensor comprising the steps:

forming a catalyst/electrolyte layer by mixing a powdered catalyst and a powdered, quasi-solid electrolyte comprising a liquid electrolyte immobilized by a high-surface-area, high-pore-volume solid and compressing the mixture;

forming an electrolyte lever by mixing a powdered, quasi-solid electrolyte comprising a liquid electrolyte immobilized by a high-surface-area, high-pore-volume solid and a binder material; and compressing the mixture together;

wherein the step of forming the catalyst/electrolyte layer further comprises mixing of a binder material with the powdered catalyst and the quasi-solid electrolyte before compressing the mixture and the step of compressing the mixture of a powdered, quasi-solid electrolyte and the binder material of the electrolyte layer is done over the compressed mixture of powdered catalyst, powdered, quasi-solid electrolyte comprising a liquid electrolyte immobilized by a high-surface-area, high-pore-volume solid and binder material of the catalyst/electrolyte layer to form an electrolyte layer bound to the catalyst/electrolyte layer.

* * * * *